United States Patent [19]
Parisi et al.

[11] Patent Number: 5,807,307
[45] Date of Patent: *Sep. 15, 1998

[54] MULTIPIECE ULTRASONIC PROBE FOR LIPOSUCTION

[75] Inventors: Tulio Parisi, San Diego; R. Kemp Massengill, Poway, both of Calif.

[73] Assignee: Sonique Surgical Systems, Inc., Escondido, Calif.

[*] Notice: The term of this patent shall not extend beyond the expiration date of Pat. No. 5,514,086.

[21] Appl. No.: 589,401

[22] Filed: Jan. 22, 1996

Related U.S. Application Data

[63] Continuation of Ser. No. 310,846, Sep. 22, 1994, Pat. No. 5,514,086.

[51] Int. Cl.⁶ .................................................. A61B 17/20
[52] U.S. Cl. ................... 604/22; 604/35; 604/902; 607/97
[58] Field of Search ................... 604/22, 31, 35, 604/264, 902, 280; 606/1, 169; 601/2; 607/97

[56] References Cited

U.S. PATENT DOCUMENTS

| | | |
|---|---|---|
| 4,808,153 | 2/1989 | Parisi . |
| 5,236,414 | 8/1993 | Takasu ........................................ 604/22 |
| 5,244,458 | 9/1993 | Takasu ........................................ 604/22 |
| 5,364,405 | 11/1994 | Zaleski . |
| 5,380,274 | 1/1995 | Nita . |
| 5,514,086 | 5/1996 | Parisi et al. . |
| 5,540,656 | 7/1996 | Pflueger et al. . |

Primary Examiner—Mark Bockelman
Attorney, Agent, or Firm—Gerald W. Spinks

[57] ABSTRACT

An ultrasonic surgical liposuction apparatus comprises a piezoelectric crystal transducer assembly is connectable to an interchangeable operative probe and a damping body attached to the probe. The probe can be hollow, if aspiration of the fatty tissue is desired, or it can be solid. The damping body is largely formed of a plastic material, to prevent the propagation of the ultrasonic waves from that portion of the probe where the damping body is mounted, to the surrounding biological tissues. Prevention of propagation of the ultrasonic energy from a portion of the probe prevents unwanted heating of that part of the surrounding tissues. The damping body can be removable or permanently affixed, such as by welding. The damping body can have a metal jacket covering a portion of the surface of the damping body, or the damping body can be entirely made of plastic. The damping body can also have an opening or a plurality of openings for aspiration of the fatty tissue.

10 Claims, 3 Drawing Sheets

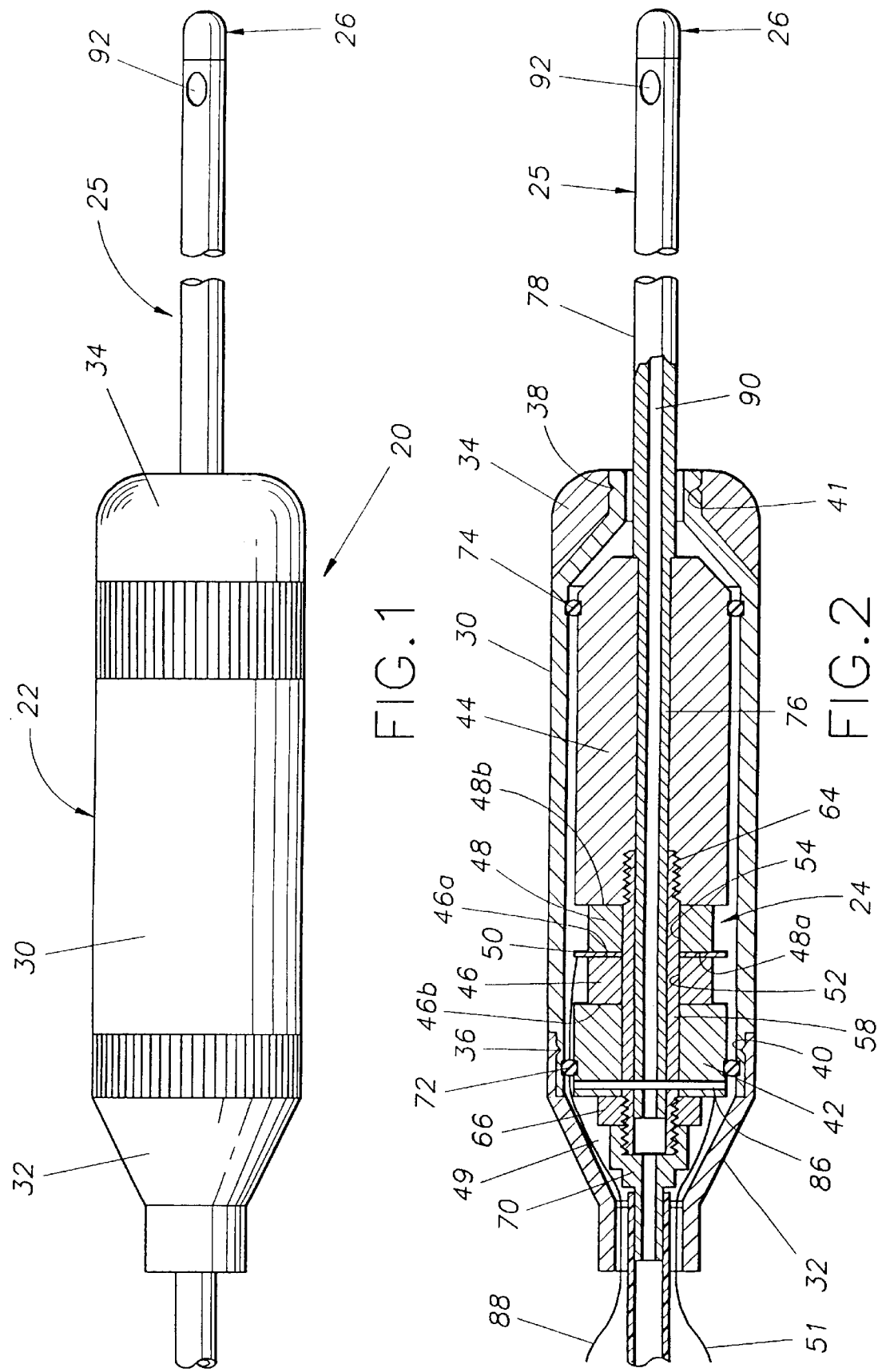

MULTIPIECE ULTRASONIC PROBE FOR LIPOSUCTION

RELATED APPLICATIONS

This is a continuation patent application of U.S. patent application Ser. No. 08/310,846, filed on Sep. 22, 1994, and entitled "Multipiece Ultrasonic Probe for Liposuction" now U.S. Pat. No. 5,514,086.

FIELD OF INVENTION

The present invention relates generally to apparatus for the surgical removal of tissue, and more particularly to a device for use in the ultrasonic removal of animal and human fatty tissue.

BACKGROUND OF THE INVENTION

This invention concerns an apparatus for liposuction. Liposuction is a type of cosmetic surgery whereby undesirable accumulations of body fat are removed by suction. Liposuction is becoming increasingly popular, and is seen by many as a way to remove quickly any undesirable body fat which may or may not be removed by the more traditional ways of diet and exercise.

The traditional liposuction techniques include the use of a cannula connected to an external source of suction. An incision is made in the area of the fat desired to be removed, the cannula is inserted into the area, and the suction is begun. The fat is then vacuumed out of the body. This procedure has its disadvantages, however, because the fat is relatively difficult to separate from the surrounding tissue. Such separation sometimes causes excessive bleeding. In addition, it is difficult to keep the operation going without stopping to clean out the cannula. Normally, the surgeon attempts to compensate for this problem by rapidly moving the cannula within the cavity, and even periodically withdrawing it to allow the fat to move through the cannula. A further problem is that the surgeon must be careful not to allow the suction to remove or injure any desirable tissues, such as muscle, blood vessels, skin, subcutaneous tissues, and the like. Therefore, the speed, safety and effectiveness of the aforementioned liposuction method leaves much to be desired, and a successful operation depends on the practitioner's exceptional skill.

It is also known to use ultrasonically vibrating and aspirating probes in the field of liposuction surgery, as described in U.S. Pat. No. 4,886,491 to the present inventors. The procedure is to introduce the vibrating probe into the area of material desired to be removed, and use the ultrasonic vibrations to physically melt the fatty tissue. The fatty tissue can be emulsified by ultrasound and aspirated through the probe, using irrigation as an adjunct. It is known that a particularly effective probe for ultrasonic liposuction is a hollow cylindrical probe with a bullet shaped tip on the distal end. The tip can be welded or otherwise affixed to the probe. Both probe and tip can be manufactured from a variety of acoustically conductive metals, including cold-rolled steel, titanium, and aluminum. In presently known devices, the probe and tip are manufactured from the same materials, or from very similar materials, to ensure effective propagation of the ultrasonic waves all the way to the tip of the probe. Propagation of the waves to the distal tip of the probe is desirable, because this causes the tip of the probe to be able to melt and emulsify fat, facilitating insertion of the probe into the fatty tissue.

In previously known liposuction techniques, before the use of ultrasound, considerable physical exertion was necessary to force the tip of the probe into the fatty tissue. This was time consuming and dangerous, and it required considerable strength on the part of the physician. The currently known ultrasonic liposuction probes are much more easily inserted into the fatty tissue, because the tip of the probe can melt the tissue in advance of the probe. This essentially melts a hole through the fatty tissue, rather than punching a hole by force. This is a much safer procedure, since it allows the physician to exercise more complete control over the advancement of the probe.

There is a disadvantage sometimes associated with an ultrasonic probe having an acoustically conductive tip, however. For instance, when the probe has been inserted into the fatty tissue near the skin or the peritoneum, resistance can be met. When resistance is met, the wattage at the tip increases, and it can increase to the point of damaging the skin or the peritoneum. During such manipulations, the heat generated at the tip of the probe may be in excess of the heat reasonably required for the melting of fat at the tip. In other words, if care is not exercised, the tip may be hotter than it needs to be, and the result can be burning of tissues, damage of muscles or blood vessels, and even penetration of membranes such as the skin or the peritoneum. Therefore, the bullet shaped tip of acoustically conductive material, while it can be very beneficial during penetration, can under certain circumstances also be detrimental.

It is an object of the present invention to provide an ultrasonic liposuction probe which does not suffer from the disadvantage of having a tip which becomes too hot for certain manipulations of the probe. It is a further object of the present invention to provide a probe which has tips which can be interchanged to facilitate different types of probe manipulations. It is a still further object of the present invention to provide an ultrasonic liposuction device which is easy to use and economical to manufacture.

SUMMARY OF THE INVENTION

An ultrasonic probe for removing tissue from a human being or other animal, particularly for removing fatty tissue, comprises a handpiece housing containing a piezoelectric crystal transducer. Interchangeable probes, each of which is formed essentially of a thin titanium or stainless steel tube, are releasably secured to the housing. A tip formed essentially of an acoustically resistive plastic such as nylon, polytetrafluoroethylene, or similar non-conductive material is removably attached to the distal end of the probe. The tip can be formed entirely of plastic, or it can have an acoustically conductive metal jacket formed around the lateral surfaces of the tip, leaving the distal end of the plastic tip exposed. Where an unjacketed tip is used, the ultrasonic energy is blocked at the junction of the probe tube and the plastic tip. There is no ultrasonic propagation beyond this junction. Where a jacketed tip is used, ultrasonic energy is efficiently transferred to the wall of the probe and to the tip jacket, where the energy is needed for the manipulations to be performed, while preventing transfer of ultrasonic energy to the exposed plastic distal end of the tip, where it could injure tissue.

The piezoelectric crystal assembly comprises several disc-shaped piezoelectric crystals, each having a central bore. The crystals are mounted in line with each other on a hollow connecting rod within the handpiece housing. The proximal end of the probe extends into the handpiece housing through the hollow connecting rod. The crystals extend along a substantial portion of the outer surface of the connecting rod, so that there is highly efficient energy transfer between the crystals and the probe, through the connecting rod. A quick release means is provided on the probe for easy changeover.

The handpiece housing is formed of a material such as metal and comprises a central cylindrical member, and a pair of end members. The end members press fit onto the central member for easy disassembly.

A probe in accordance with the present invention, used in conjunction with the ultrasonic device, comprises a thin walled, hollow cylindrical metal tube. A bullet shaped tip is threaded to the distal end of the probe. The tip is largely constructed of a material having substantially more acoustic impedance than the probe, such as a plastic. Alternatively, rather than using materials having differing acoustic resistivities for the probe and the tip, the desired difference in acoustic impedance could be achieved by appropriate structural design of the probe and the tip. Specifically, the structure of the probe could be designed to promote propagation of longitudinal ultrasonic waves, using well known design techniques, while the structure of the tip could be designed to impede the propagation of the ultrasonic waves.

The probe could also be solid, rather than hollow, if aspiration of the melted fatty tissue is not required. If the probe is hollow, it can have a lateral opening for aspiration, or there could be an opening through the tip. As mentioned before, the tip can be made entirely of plastic, or it can have a plastic core and a metal jacket which leaves the distal end of the plastic core exposed.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a plan view of an ultrasonic liposuction device incorporating a probe and tip according to the present invention;

FIG. 2 is a longitudinal section view of the device shown in FIG. 1;

DESCRIPTION OF PREFERRED EMBODIMENTS

Figure 3:
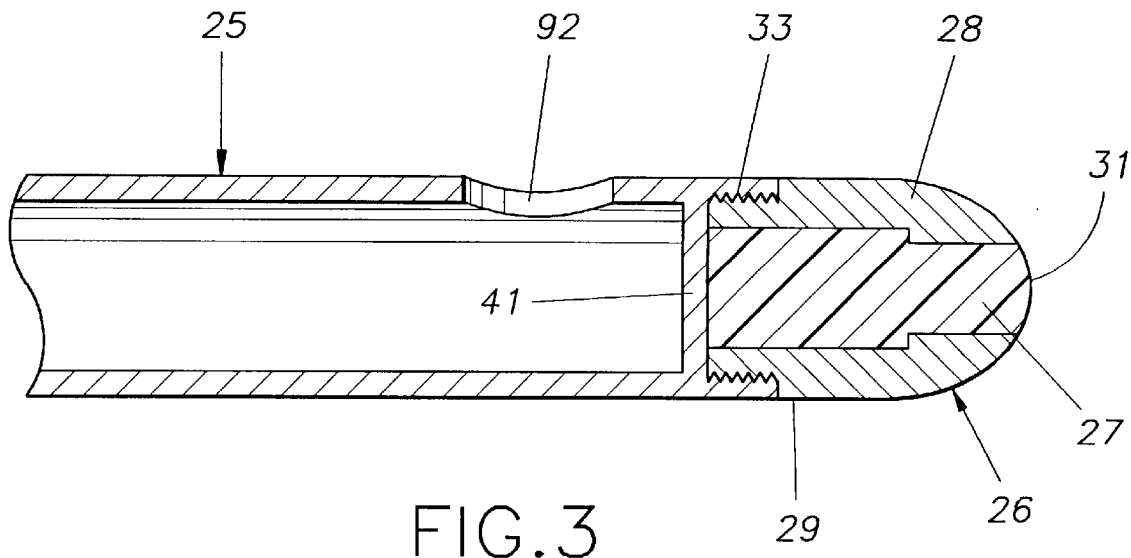
FIG. 3 is a longitudinal section view of the distal end of a first embodiment of the probe and tip of the present invention, showing a hollow probe and a metal jacketed plastic tip.

Referring to FIGS. 1 and 2, an ultrasonic liposuction assembly 20, used for ultrasonically removing fatty tissue, comprises a handpiece or housing 22 containing a piezoelectric transducer assembly 24 for imparting ultrasonic vibrations to a probe 25 formed preferably of titanium or cold-rolled steel. A tip 26, formed of plastic or plastic and metal, is mounted on the distal end of the probe 25. As shall be described in more detail below, the probe 25 extends through a central bore in the piezoelectric transducer 24. The assembly shown here is an example of a type of transducer assembly which can be used with the probe and tip of the present invention, but other types can be used as well.

The housing 22, formed preferably of aluminum, includes a hollow cylindrical central member 30 and two end members 32, 34. Annular recesses 36, 38 are formed in the central member 30, and the end members 32, 34 contain annular ribs 40, 41, respectively. The ribs 40, 41 fit into the annular recesses 36, 38. The end members 32, 34 are retained to the center member 30 by these corresponding annular ribs 40, 41 and recesses 36, 38, when the end members 32, 34 are press-fitted to the central member 30.

The transducer assembly 24 comprises a first piezoelectric crystal 46 and a second piezoelectric crystal 48 located within the housing 22 on opposite sides of a disc-shaped electrode 50. The crystals 46, 48 and the electrode 50 are seated in housing 22 between two body members 42, 44 formed of an electrically conductive material, such as titanium. The body members 42, 44, the crystals 46, 48, and the electrode 50, are maintained in axial alignment with each other by the connecting rod 58, which passes through two bores 52, 54 in the crystals 46, 48 as well as through an aperture in the electrode 50.

The connecting rod 58 is a hollow tube also formed of electrically conductive material, such as titanium, and it has two threaded ends. One end of the rod 58 is coupled to a threaded bore of a collar 70, and the other end of the rod 58 is coupled to a threaded bore within the distal body member 44. A nut 66 is also threaded onto the first end of the connecting rod 58 in abutment with the proximal body member 42 and the collar 70, for maintaining the proximal body member 42 against the proximal crystal 46. The bore of the proximal body member 42 is unthreaded.

The piezoelectric transducer assembly 24 is prestressed within the housing 22 by compression between the body members 42, 44. The body members 42, 44 are urged against the transducer assembly 24 by first tightening the nut 66 on the connecting rod 58 until the assembly 24 is compressed so as to generate a maximum ultrasonic vibration output. This can be done by monitoring the vibration output of the probe 25 as the nut 66 is tightened, but in practice, the nut is tightened by an amount determined by experience to provide substantial ultrasonic vibrational output from the crystal assembly 24. The nut 66 is then locked in place by the collar 70.

The body members 42 and 44 are electrically and mechanically insulated from the housing 22 by two O-rings 72, 74. The O-rings 72, 74 float the body members 42, 44 within the housing 22, so that during ultrasonic vibration of the probe 25, vibration is not coupled to the housing 22, thereby permitting more precise control of the probe 25 by a surgeon.

The probe 25 is an elongated, hollow titanium tube having a proximal section 76 and a distal section 78. A shoulder interfaces the proximal section 76 and the distal section 78. The proximal end of the proximal section 76 contains a keyhole slot for snap fitting to a corresponding transverse pin 86 in the housing 22.

The probe 25 is inserted into the housing 22 through the body members 42, 44 and the connecting rod 58. The pin 86 is mounted within the proximal body member 42 and the connecting rod 58, through a radial aperture. The proximal section 76 of the probe 25 snap fits to the pin 86 by rotating the probe 25 until there is alignment between the keyhole slot in the probe 25 and the pin 86, and then snapping the probe 25 onto the pin 86. The shoulder of the probe 25 is maintained in abutment with the distal end of the distal body member 44.

A high frequency source (not shown) of alternating voltage is supplied to the transducer assembly 24 through an opening 49 in the end member 32 of the housing 22. A first wire 88 from one terminal of the voltage source is connected to the electrode 50 and a second wire 51 from the opposite terminal of the voltage source is connected to the proximal body member 42. The inner faces 46a, 48a of the crystals 46, 48 at the electrode 50 thus receive one polarity of the high frequency alternating voltage, and the outer faces 46b, 48b of the crystals 46, 48 receive an opposite polarity voltage. The body members 42, 44, along with the connecting rod 58, provide a circuit between the outer faces 46b, 48b of the crystals 46, 48.

With an alternating voltage of an ultrasonic frequency applied between the body members 42, 44 and the electrode 50, the piezoelectric crystals 46, 48 vibrate in a known manner at the ultrasonic frequency. The frequency is in the range of 20 KHz to 65 KHz, and it is preferably approximately 20 to 40 KHz. The amplitude of the ultrasonic vibration is from 0 to 0.015 inch, and preferably approximately 0.002 to 0.005 inch when measured at the tip of the probe. Ultrasonic vibrations from the crystals 46, 48 are mechanically coupled to the connecting rod 58, and the vibrations in turn are mechanically coupled from the connecting rod 58 to the proximal section 76 of the probe 25.

The probe 25 also contains a longitudinal channel 90 for aspirating melted and emulsified fatty tissue through the probe 25 from an opening 92 near the distal end of the probe 25. The aspirated tissue is drawn by suction through a conduit secured to the proximal end of the housing 22.

As aforementioned, in accordance with the embodiment shown, the probe 25 is releasably secured to the housing 22 by a keyhole slot in the probe 25 that snap fits to the transverse pin 86. Alternatively, a set of threads can be formed on the proximal section 76 of the probe 25, in place of the keyhole slot. A corresponding set of threads can be formed on the inner wall of the connecting rod 58, and the probe 25 can extend into the connecting rod 58, with the threads engaging each other.

In order to connect the threaded probe 25 to the housing 22, the surgeon simply inserts the proximal end of the probe 25 into the mouth of the distal end member 34 until the threads on the probe 25 contact the threads in the connecting rod 58. Then the surgeon twists the probe 25 until the threads are engaged and tightened.

Referring now to FIG. 3, a longitudinal section of a preferred embodiment of the distal end of the probe 25 and tip 26 of the present invention is shown. This embodiment is most useful where the probe apparatus will be used to penetrate the fatty tissue, but it will also be used to perform other manipulations, such as sidewise movement. It is, therefore, a combination probe apparatus with a tip 26 active enough to penetrates but having an acoustically inactive distal end to protect tissues during other manipulations. In this embodiment, the probe 25 is a longitudinal, hollow, cylindrical tube, having one or more lateral openings 92 through the tube wall near the distal end of the probe 25. The probe 25 can be constructed of a material, preferably a metal, having a relatively low acoustic impedance. Examples of suitable metals include, without limitation, cold-rolled steel, titanium, and aluminum, with titanium being preferred. An end wall 41 closes the distal end of the probe 25.

A bullet shaped tip 26 is removably mounted to the distal end of the probe 25 by threads 33. A fixed, non removable configuration of the bullet tip can be obtained by applying a permanent weld between the bullet tip and the adjacent cannula. The tip 26 shown in this embodiment comprises a solid tip body 27 and an outer metal jacket 28. The outer metal jacket 28 covers the lateral surfaces 29 of the tip 26, while leaving the distal end 31 of the tip body 27 exposed. The tip body 27 is constructed of a material, preferably a plastic, which has an acoustic impedance substantially greater than that of the probe 25. Examples of suitable materials for the tip body 27 would include, without limitation, nylon, polyurethane, polyethylene, and polytetrafluorethylene, with polytetrafluorethylene being preferred. Examples of suitable materials for the metal jacket 28 would be the same as for the probe 25.

The metal jacket 28 should cover only a portion of the distal end of the tip 26, in order to facilitate insertion of the probe 25 into the fatty tissue. The covered portion should range from approximately the outer one fourth to approximately the outer one half of the radius of the projected area of the tip 26, leaving the central portion of the tip body 27 exposed. In other words, if the tip 26 has an overall radius R. the exposed central portion of the tip body 27 should have a radius of between ½ R and ¾ R. The preferred radius of the exposed central portion of the tip body 27 in most cases is approximately ⅔ R. The degree of exposure of the tip body 27 can be varied according to the intended use of the tip 26, by exchanging tips 26. For instance, greater exposure of the tip body 27 might be possible in areas where the fatty tissue is less dense and penetration is easier, with greater coverage by the metal jacket 28 being called for in areas where the fatty tissue is more dense and penetration is more difficult. The greater the degree of exposure of the plastic tip body 27, the safer the tip 26 will be, but the more difficult penetration will be through fatty tissue.

Figures 4, 5:
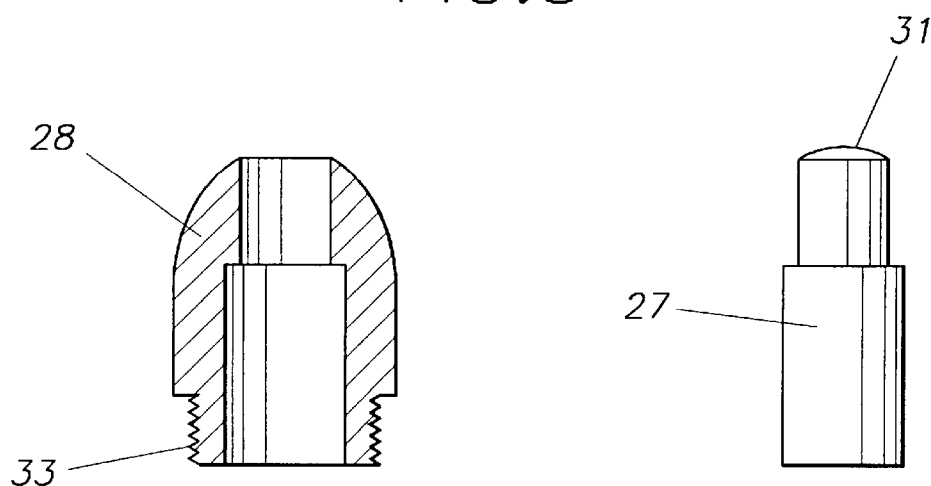
FIG. 4 is a longitudinal section view of a metal jacket incorporated into the tip of the embodiment shown in FIG. 3.
FIG. 5 is an elevation view of the body of the tip shown in FIG. 3.

FIG. 4 shows a section view of the metal jacket 28 of the tip 26 shown in FIG. 3. The base of the jacket 28 is formed with a reduced outer diameter and externally threaded to match internal threads in the distal end of the probe 25. The outer diameter of the jacket 28 matches the outer diameter of the probe 25. A generally cylindrical cavity is formed inside the jacket 28, with a stepped configuration, if required to allow extension of the desired portion of the distal end of the jacket 28 over the distal end of the tip body 27. The configuration of the cylindrical cavity is designed in accordance with known acoustic design principles to ensure propagation of the ultrasonic waves to the distal end of the jacket 28.

FIG. 5 shows the plastic, generally cylindrical tip body 27 with a rounded distal end 31, for use in the tip 26 shown in FIG. 3. This embodiment of the tip body 27 is sized and shaped to fit closely within the metal jacket 28. The rounded distal end 31 blends with the contour on the distal end of the metal jacket 28 and facilitates passage of the tip 26 through fatty tissue.

Figure 6:
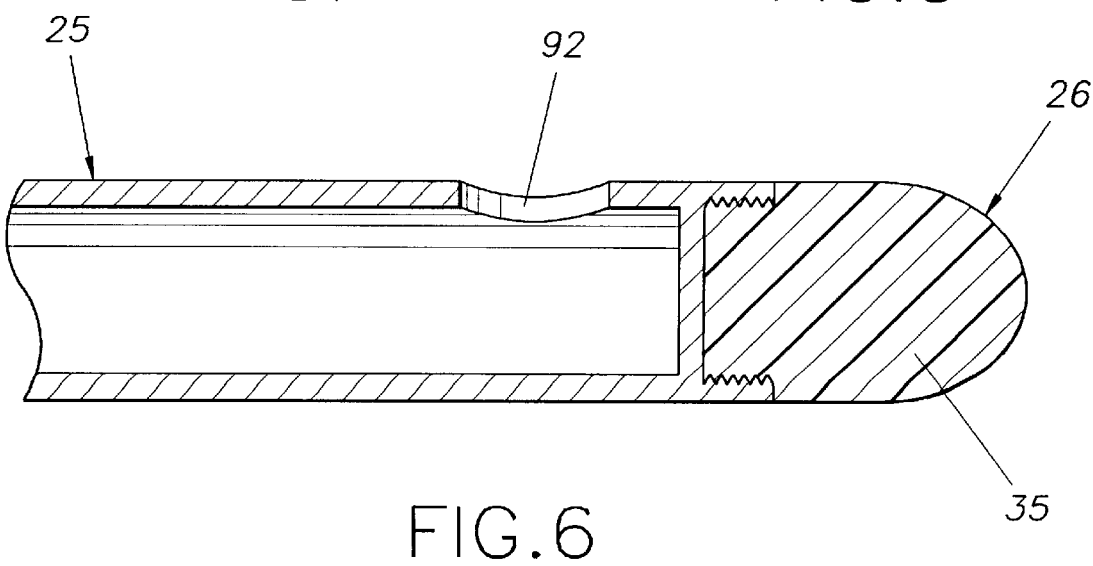
FIG. 6 is a longitudinal section view of the distal end of a second embodiment of the probe and tip of the present invention, showing a solid plastic tip.

FIG. 6 shows an alternative embodiment of the distal end of the probe 25 and the tip 26. This embodiment is most useful in applications where the tip 26 will not need to melt the fatty tissue in order to penetrate, such as where a penetration has already been formed. In this embodiment, the probe 25 is still hollow, with one or more lateral openings 92 for the aspiration of fatty tissue. The tip 26, on the other hand, is a solid plastic tip body 35, with no metal jacket. The distal end of the tip body 35 is rounded, to assist in penetration through existing holes, and to avoid unnecessary damage to surrounding tissues. The outer diameter of the tip 26 closely matches the outer diameter of the probe 25.

Figure 7:
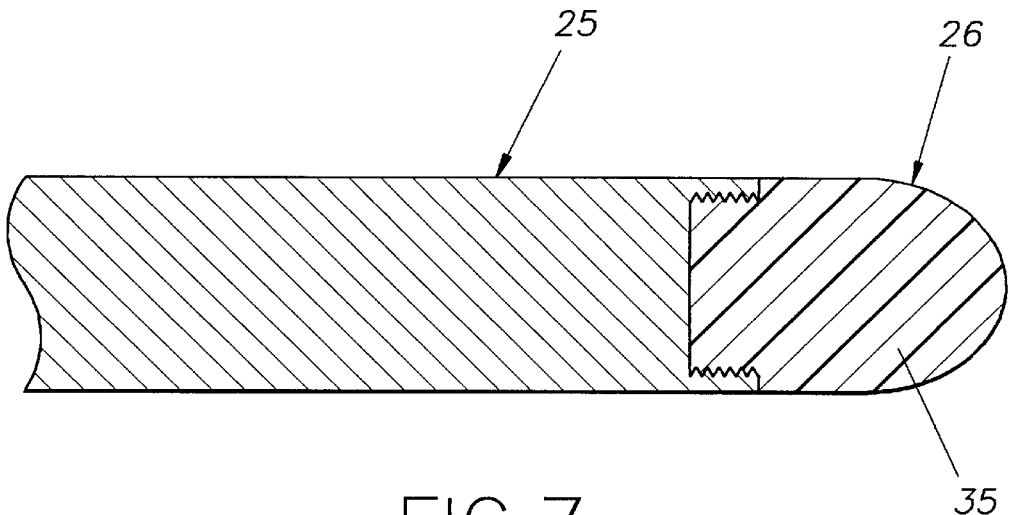
FIG. 7 is a longitudinal section view of the distal end of a third embodiment of the probe and tip of the present invention, showing a solid probe and a solid plastic tip.

FIG. 7 shows still another embodiment of the probe apparatus, useful in applications where no fatty tissue will be aspirated through the probe 25, such as where the fatty tissue is simply being melted for smoothing purposes. The probe 25 is a solid longitudinal cylinder, with a threaded recess formed in the distal end. A solid unjacketed tip body 35 is threaded into the distal end of the probe 25, with the outer diameter of the tip 26 closely matching the outer diameter of the probe 25.

Figure 8:
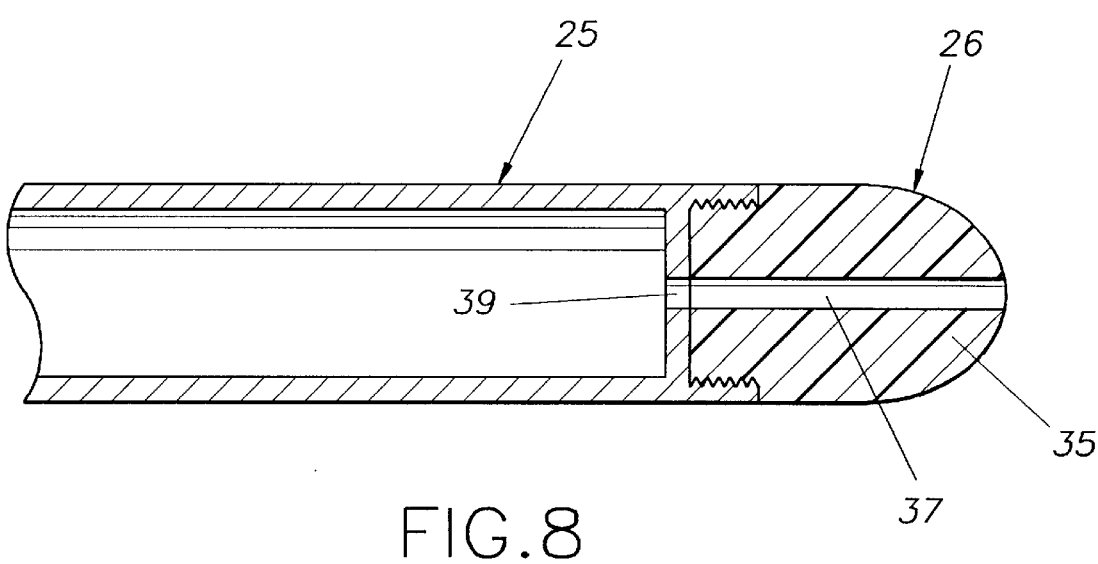
FIG. 8 is a longitudinal section view of the distal end of a fourth embodiment of the probe and tip of the present invention, showing a hollow probe and a solid plastic tip with an aspiration hole.

FIG. 8 shows yet another embodiment, where the tip body 35 has a through hole 37, leading from the exterior of the probe assembly to the interior of the probe 25, via hole 39 in the end wall 41. The tip body 35 is solid and unjacketed, and the outer diameter of the tip 26 closely matches the outer diameter of the probe 25. As fatty tissue is melted and emulsified, it can be aspirated through the hole 37. This embodiment might be useful in applications where lateral aspiration might cause a problem.

Figure 9:
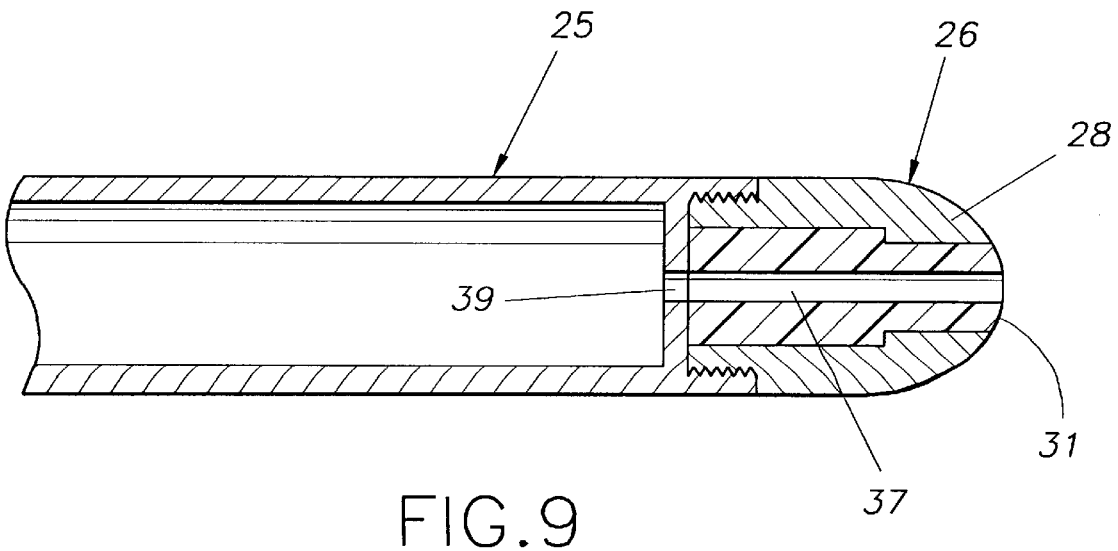
FIG. 9 is a longitudinal section view of the distal end of a fifth embodiment of the probe and tip of the present invention, showing a hollow probe and a metal jacketed plastic tip with an aspiration hole.

FIG. 9 shows a further embodiment, where the tip 26 has a metal jacket 28, and where the tip body 31 has a generally cylindrical configuration and a through hole 37. As in the other embodiments, the outer diameter of the tip 26 closely matches the outer diameter of the probe 25. This particular embodiment might be useful where penetration of fatty tissue will be required, but where lateral aspiration might cause a problem.

While the particular Multipiece Ultrasonic Probe for Liposuction as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A device for removal of fatty tissue, comprising:
   a handpiece;
   a probe attached to said handpiece, said probe being constructed of ultrasonically conductive material for delivering ultrasonic energy to surrounding tissue along the outer surface of said probe;
   an ultrasonic means acoustically connected to said probe for imparting ultrasonic vibrations to said probe; and
   a damping body externally mounted on a distal portion of said outer surface of said probe, the proximal portion of the probe being exposed for tissue contact, said external damping body being exposed for contact with surrounding tissue in an area of the probe where application of ultrasonic energy to surrounding tissue is not desired, said damping body having an acoustic impedance substantially greater than said probe, to effect the damping of longitudinal vibrations of ultrasonic energy in said portion of said outer surface of said probe.

2. A device as claimed in claim 1, wherein:
   said probe is constructed from a first material having a first acoustic impedance; and
   said damping body is constructed from a second material having a second acoustic impedance, said second acoustic impedance being greater than said first acoustic impedance.

3. A device as claimed in claim 2, wherein:
   said first material is a metal; and
   said second material is a plastic.

4. A device as claimed in claim 3, wherein:
   said metal is titanium; and
   said plastic is polytetrafluorethylene.

5. A device as claimed in claim 1, wherein said probe is solid.

6. A device as claimed in claim 1, wherein said probe is hollow.

7. A device as claimed in claim 6, further comprising an opening in said probe for aspiration of said fatty tissue.

8. A device as claimed in claim 6, further comprising an opening in said damping body for aspiration of said fatty tissue.

9. A device as claimed in claim 1, further comprising a jacket partially covering said damping body, said jacket being acoustically connected to said ultrasonic means, said jacket having an acoustic impedance approximately matching said acoustic impedance of said probe.

10. A device as claimed in claim 9, wherein said acoustical connection between said ultrasonic means and said jacket is achieved by means of said probe.

* * * * *